(12) United States Patent
MacFarlane et al.

(10) Patent No.: US 9,545,223 B2
(45) Date of Patent: Jan. 17, 2017

(54) FUNCTIONAL NEAR INFRARED SPECTROSCOPY IMAGING SYSTEM AND METHOD

(71) Applicant: Board of Regents, The University of Texas System, Austin, TX (US)

(72) Inventors: Duncan MacFarlane, Dallas, TX (US); Chester Wildey, Euless, TX (US); Georgios Alexandrakis, Arlington, TX (US); Bilal Khan, Fort Worth, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 773 days.

(21) Appl. No.: 13/687,700

(22) Filed: Nov. 28, 2012

(65) Prior Publication Data

US 2013/0090541 A1    Apr. 11, 2013

Related U.S. Application Data

(63) Continuation-in-part of application No. 13/410,187, filed on Mar. 1, 2012, now abandoned.

(Continued)

(51) Int. Cl.
*A61B 5/1455* (2006.01)
*A61B 5/00* (2006.01)

(52) U.S. Cl.
CPC ......... *A61B 5/14553* (2013.01); *A61B 5/0042* (2013.01); *A61B 5/0075* (2013.01);
(Continued)

(58) Field of Classification Search
CPC ... A61B 5/0059; A61B 5/0073; A61B 5/1455; A61B 5/14551; A61B 5/14552; A61B 5/14532
(Continued)

(56) References Cited

U.S. PATENT DOCUMENTS 5,497,769 A    3/1996  Gratton et al.
5,586,554 A *  12/1996  Maki .................. A61B 5/0073
                                                    600/407

(Continued)

OTHER PUBLICATIONS

Khan, Bilal, "Functional Near Infrared Spectroscopy for the Assessment of Motor Cortex Plasticity in Pediatric Subjects Affected by Cerebral Palsy" M.Sc. Dissertation, University of Texas at Arlington, published Aug. 2009.

(Continued)

*Primary Examiner* — Tse Chen
*Assistant Examiner* — Chu Chuan (JJ) Liu
(74) *Attorney, Agent, or Firm* — Schultz & Associates, P.C.

(57) ABSTRACT

Disclosed is a functional NIRS imaging system including an elastomeric cap, a set of transmit optical fibers and a set of receive optical fibers terminating on the inside surface of the elastomeric cap. A pair of light sources combines to produce a collimated light beam at two wavelengths. An optical modulation system, converts the light beam into a plurality of probe light beams, modulates the plurality of probe light beams and directs each probe light beam into a transmit fiber. An optical detection system accepts scattered photons from subcutaneous tissue underneath the elastomeric cap as a plurality of collected light beams and converts them into a time series of electronic images, stores the electronic images into the memory and processes the electronic images using. The system displays the resulting image on a display as a hemoglobin oxygen saturation map.

1 Claim, 10 Drawing Sheets

Related U.S. Application Data

(60) Provisional application No. 61/464,305, filed on Mar. 2, 2011.

(52) U.S. Cl.
CPC ..... *A61B 5/6803* (2013.01); *A61B 2562/0238* (2013.01); *A61B 2562/046* (2013.01)

(58) Field of Classification Search
USPC ........ 600/310, 322, 323, 328, 340, 473, 476
See application file for complete search history.

(56) References Cited

U.S. PATENT DOCUMENTS

| | | | |
|---|---|---|---|
| 5,772,587 A | 6/1998 | Gratton et al. | |
| 5,803,909 A * | 9/1998 | Maki | A61B 5/0059 600/310 |
| 6,078,833 A | 6/2000 | Hueber | |
| 6,192,261 B1 | 2/2001 | Gratton et al. | |
| 7,616,984 B2 | 11/2009 | Barbour et al. | |
| 7,778,693 B2 | 8/2010 | Barbour et al. | |
| 7,983,740 B2 | 7/2011 | Culver et al. | |
| 2006/0184047 A1 * | 8/2006 | Yamashita | A61B 5/0059 600/476 |
| 2006/0247514 A1 | 11/2006 | Panayuk et al. | |
| 2008/0154126 A1 | 6/2008 | Culver et al. | |
| 2008/0306337 A1 | 12/2008 | Livingston et al. | |
| 2009/0002794 A1 * | 1/2009 | Weir | A61B 1/00096 359/213.1 |
| 2010/0056928 A1 | 3/2010 | Zuzak et al. | |

OTHER PUBLICATIONS

Zuzak, Karel J., et al., "Characterization of a Near-Infrared Laparoscopic Hyperspectral Imaging System for Minimally Invasive Surgery", Analytical Chemistry, vol. 79, No. 12, Jun. 15, 2007, pp. 4709-4715.

Zuzak, Karel J., et al., "Intraoperative Bile Duct Visualization using Near-Infrared Hyperspectral Video Imaging", American Journal of Surgery, vol. 195 (2008), pp. 491-497.

Khan, Bilal, et al. "Functional Near Infrared Brain Imaging with a Brush-Fiber Optode to Improve Optical Contact on Subjects with Dense Hair", Photonic Therapeutics and Diagnostics VII, Proc. of SPIE vol. 7883, (2011) 78834V1-V11.

* cited by examiner

FIG. 5

| Transmit fiber index | DMD mirror index | DMD mirror pos x | DMD mirror pos y | Cap pos x | Cap pos y | Image pos x | Image pos y | Optical loss | Time slot | Range |
|---|---|---|---|---|---|---|---|---|---|---|
| 1 | | | | | | | | | | |
| 2 | | | | | | | | | | |
| 3 | | | | | | | | | | |
| . | | | | | | | | | | |
| . | | | | | | | | | | |
| f | | | | | | | | | | |

| Receive fiber index | Cap pos x | Cap pos y | Image pos x | Image pos y | Optical loss |
|---|---|---|---|---|---|
| 1 | | | | | |
| 2 | | | | | |
| 3 | | | | | |
| . | | | | | |
| . | | | | | |
| f | | | | | |

181, 182, 183, 184, 185, 186; 180

FUNCTIONAL NEAR INFRARED SPECTROSCOPY IMAGING SYSTEM AND METHOD

CROSS-REFERENCE TO RELATED APPLICATIONS

This application is a continuation-in-part which claims priority to U.S. patent application Ser. No. 13/410,187 filed on Mar. 1, 2012 which claims priority to provisional application No. 61/464,305 filed on Mar. 2, 2011.

FIELD OF THE INVENTION

The present disclosure relates to measurement and monitoring of near infrared images of subcutaneous matter. The field of the invention includes functional near infrared spectroscopic imaging of the brain and muscle tissues and includes dynamic imaging of hemoglobin oxygen concentration.

BACKGROUND OF THE INVENTION

Non-invasive methods of monitoring brain activity have long been sought. More recently, systems that allow a patient to perform activities while monitoring brain activity, known as functional monitoring have been sought which allow neurological and psychological study of the patient. Many types of diagnoses and studies are made possible including studies that involve brain development in children, brain activity in mentally deficient patients, patients that have experienced brain damage or concussions, conditions such as migraines, and in the elderly, conditions such as Alzheimer's disease.

The technique of near infrared spectroscopy and functional near infrared spectroscopy have been shown to be useful in obtaining images of subcutaneous matter including fluids and solid matter. Near infrared spectroscopy is accomplished by transmitting light through the skin from a near infrared light source and into the subcutaneous tissue where it is scattered and absorbed. The scattered light is detected by a detector, usually coupled to an optical fiber placed a short distance away from the transmission source. Near infrared images of subcutaneous matter are generally wavelength dependent due to the light absorption characteristics of water, of oxygenated hemoglobin (HbO) and of deoxygenated hemoglobin (Hb). Observation of three dimensional spatial variations of hemoglobin concentration is possible using multiple wavelengths of light. Most often, lasers or LED sources in the ranges of 690 nm to 830 nm are employed.

Near-infrared spectroscopy has shown to be a promising tool in breast imaging for early detection of breast cancer, peripheral vasculature for diagnostics relating to peripheral blood flow and arterial health which are common issues in diabetics, and in related research applied to animals.

Depth of the imaging field is in the range of centimeters: about 3 to 4 cm for brain imaging, about 10-12 cm for breast imaging, and about 6 to 8 cm for the peripheral body such as the arms and legs.

Commercial systems exist in the art. FIG. 1A shows a typical prior art system. Patient 1 wears cap 2. The cap includes optical fibers held in close proximity to the patient's skull. The optical fibers include bundle of transmit fibers 3 and bundle of receive fibers 4. Bundle of transmit fibers 3 are connected to a set of lasers on a set of transmitter cards 5. Bundle of receive fibers 4 are connected to a corresponding set of optical detectors on a set of receiver cards 6. The set of transmitter cards and the set of receiver cards are controlled by computer 8 having memory 7. The computer operates to collect data from the receiver cards and process it using image processor 10 to determine various imaging data. For example, hemoglobin concentration may be determined as a function of position on the skull and at various depths within the brain. Display 9 is used to display the processed images and hemoglobin concentration maps.

In FIG. 1B, a prior art transmitter card is shown. The transmitter card includes a set of lasers 21 operating at the two wavelengths, 690 nm and 830 nm. Typically, there are four lasers of each wavelength on a card, where each laser includes fiber pigtail 25 to an external fiber optic connector 22. Fibers 27 from bundle of transmit fibers 3 are separated. Each fiber includes a connector which is mated to connector 22.

In FIG. 1C, a prior art receiver card is shown. The receiver card includes a set of detectors 18. Avalanche photodiode detectors (APD) are typically included for detecting low light levels. In most cases, four photodetectors are included on each card. Each photodetector includes fiber pigtail 20 to external fiber optic connector 23. Fibers 28 from the bundle of receive fibers are separated. Each fiber terminated with a fiber connector which is mated to external fiber optic connector 23. The transmitter cards and the receiver cards are connected to and interact with the computer.

FIG. 2 shows a prior art diagram depicting a detail of cap 2 in operation. A patient's head including skin 39 covering subcutaneous fluid 40 is shown. Membrane 38 supports and positions input fiber 30, and output fibers 31-36. Near infrared light, when injected through input fiber 30 is scattered by the subcutaneous fluid in all directions. However, certain scattering paths allow for the light to propagate into the output fibers. An example is central blood flow artifact 48. Light path 44 captures light from input fiber 30 to output fiber 31. Light path 42 captures light from input fiber 30 to output fiber 32. Light path 43 captures light from input fiber 30 to output fiber 33. Light path 44 captures light from input fiber 30 to output fiber 34. Light path 45 captures light from input fiber 30 to output fiber 35. Light path 46 captures light from input fiber 30 to output fiber 36. The "banana" shaped light paths are statistical in nature describing paths that photons take while propagating in the subcutaneous fluid from the light source towards the detector. In so doing, some of the photons are absorbed. The absorption is exponentially related to the path length and to artifacts. In particular, photons propagating in the region of central blood flow artifact 48 will experience a higher rate of absorption as determined by the extinction coefficient of the material comprising central blood flow artifact 48. Thus, light detected in output fibers 33 and 35, in particular, will be less than their counterparts, output fibers 34 and 36, respectively. Also, note that output fibers 35 and 36 probe deeper into the subcutaneous fluid than output fibers 31 and 32, for example.

In the prior art, Gratton et al. in U.S. Pat. No. 5,497,769 discloses the quantitative determination of various materials in highly scattering media such as living tissue in an external, photometric manner by the use of a plurality of light sources positioned at differing distances from a sensor. The light from said sources is amplitude modulated in accordance with conventional frequency domain fluorometry techniques where the gain of the sensor is modulated at a frequency different from the frequency of the light modulation. The sensor heads carry eight light sources and the light passing through the living tissue may be transmitted to a photomultiplier detector by an optical fiber.

Barbour et al., in U.S. Pat. No. 7,778,693 discloses a time series of optical tomography data obtained for a target tissue site in a human using a near infrared optical wavelength to observe properties of the vasculature of the human. A target placed in an imaging head is exposed to optical energy from combined sources. A source demultiplexer is controlled by a computer to direct the optical energy source fibers sequentially. The imaging head contains a plurality of source fibers and detector fibers for transmitting and receiving light energy, respectively. The optical energy entering the target at one location is scattered and may emerge at any location around the target where it is collected by detector fibers. The imaging process is repeated so as to deliver optical energy sequentially, a measurement being obtained for detected emerging optical energy at each detector for each emitting source fiber. Barbour et al. discloses a system with 32 detection channels.

In U.S. Pat. No. 7,983,740 to Culver et al., an imaging system for diffuse optical tomography is disclosed including a dense grid of light emitting diodes as sources wherein each light emitting diode has individual, isolated power to reduce crosstalk and each detector channel has a dedicated avalanche photo diode. The separation of signals is carried out through decoding frequency encoding.

These prior art systems suffer from a number of deficiencies. A first deficiency is in the size and portability of the system. As researchers and physicians have gained experience with these systems, they have seen the need for a larger numbers of detectors and sources in order to increase resolution. Current systems have as many as 128 detectors or transmitters. Such a system would require a fairly large rack of equipment and substantial space to operate. Furthermore, the sheer numbers and cost of the electronics become prohibitively large. Second, prior art systems operate at frame rates of about 2.5 Hz or less, at low resolutions and small coverage areas. For larger coverage areas the frame rates deteriorate to less than 1 Hz.

A compact near infrared hyperspectral imaging system is disclosed by Livingston et al. in U.S. Patent Application Publication No. 2008/0306337 that discloses an apparatus and method of the use of a hyperspectral surgical laproscope comprising a liquid crystal tunable filter mounted on the laproscope, positioned to collect back-reflected light from a target, and focal plane array also mounted on the laproscope to image light reflected from the target.

A digital light processing hyperspectral imaging apparatus is disclosed by Zuzak et al. in U.S. Patent Application Publication No. 2010/0056928, the system including an illumination source adapted to output a light beam, the light beam illuminating a target, a dispersing element arranged in the optical path and adapted to separate the light beam into a plurality of wavelengths, a digital micromirror array adapted to tune the plurality of wavelengths into a spectrum, an optical device having a detector and adapted to collect the spectrum reflected from the target and arranged in the optical path and a processor operatively connected to and adapted to control at least one of these components and further adapted to output a hyperspectral image of the target.

However, these prior art systems only provide images of the spectral response of the tissue area and depth illuminated as a whole without regard for localized photonic excitation and scattering. As a result, lateral and depth spatial resolutions as well as image contrast of these systems remain limited.

SUMMARY OF THE INVENTION

A functional NIRS imaging system for hemodynamic imaging of subcutaneous tissue is disclosed utilizing a computer with a processor, a memory, a persistent storage device and a display. The system includes an elastomeric cap; a first optical fiber bundle terminating together at an entrance plane and terminating dispersively on the inside surface of the elastomeric cap; a second optical fiber bundle terminating together at an exit plane and terminating dispersively on the inside surface of the elastomeric cap. The system has a first light source producing a first light beam at a first wavelength and a second light source producing a second light beam at a second wavelength, both controlled by the computer. An optical combiner combines the first light beam and the second light beam into a third light beam. An optical collimator collimates the third light beam into a fourth light beam. An optical modulation system, controlled by a modulation controller, accepts the fourth light beam, converts the fourth light beam into a plurality of probe light beams, modulates the plurality of probe light beams and programmatically directs each probe light beam in the plurality of probe light beams into a corresponding optical fiber in the optical fiber bundle.

An optical detection system controlled by the first processor is connected to the first memory, which accepts a plurality of collected light beams from the second optical fiber bundle, converts the plurality of collected light beams into a time series of electronic images and stores the time series of electronic images into the memory.

The computer converts the stored time series of electronic images into a set of hemoglobin oxygen saturation level images, programmatically displays the set of hemoglobin oxygen saturation level images on the display and stores the set of hemoglobin oxygen saturation level images in the persistent storage device.

The first light source and the second light source may be controlled to alternate the wavelength of the fourth light beam between the first wavelength and the second wavelength.

In a preferred embodiment, the functional NIRS system modulates the plurality of probe light beams with a time division multiplexing scheme in which a probe light beam is assigned to a time slot selected from a series of time slots.

In an alternate embodiment, the functional NIRS system modulates the plurality of probe light beams with a frequency division multiplexing scheme in which a probe light beam is assigned to a modulation frequency selected from a set of modulation frequencies.

In another aspect of the functional NIRS system, a first raw image is stored by the optical detection system in the first memory and corresponds to the fourth light beam having the first wavelength; and, a second raw image is stored by the optical detection system in the first memory and corresponds to the fourth light beam having the second wavelength. In a related aspect, the first raw image is taken in the first half of a time slot and the second raw image is taken in the second half of the time slot.

The functional NIRS system produces a first set of intermediate images associated to a subset of optical fibers in the first bundle of optical fibers and derived from the first raw image. The functional NIRS system further produces a second set of intermediate images associated to the subset of optical fibers and derived from the second raw image. A first resultant image is derived from the first set of intermediate images and a transformation matrix and stored in the first memory. A second resultant image is derived from the second set of intermediate images and the transformation matrix and also stored in the first memory.

The functional NIRS system further produces a hemoglobin saturation map derived from the first resultant image and the second resultant image which is stored in the persistent storage device.

In one embodiment, the optical modulation system includes a spatial light modulator and an optical lens and in a first aspect of this embodiment the spatial light modulator is a MEMS digital mirror device. In a second aspect of this embodiment the spatial light modulator is a liquid crystal light modulator.

The optical detection system may include an optical lens and an optical detector array. In a first aspect of the optical detection system, the optical detector array includes an array of avalanche photodiodes. In an alternate embodiment, an array of regular photodiodes is employed. In a second aspect of the optical detection system, the optical detector array is a multi-anode photomultiplier tube. In a third aspect of the optical detection system, the optical detector array a CMOS imaging device. In a fourth aspect of the optical detection system, the optical detector array is a charge-coupled imaging device.

In another embodiment, the second optical fiber bundle terminates on the inside surface of the elastomeric cap in a packed hexagonal pattern with each receive optical fiber in the second optical fiber bundle located at a vertex of a hexagon. In one aspect of this embodiment each optical fiber in the first optical fiber bundle terminates on the inside surface of the elastomeric cap near the center of each hexagon in the packed hexagonal pattern. In another aspect of this embodiment, each hexagon in the packed hexagonal pattern has a characteristic size of about 2 millimeters. In another aspect of this embodiment, the first optical fiber bundle comprises about 4000 optical fibers and the second optical fiber bundle comprises about 8500 optical fibers and the elastomeric cap is approximately the size of a human scalp.

The functional NIRS system utilizes a set of calibration data stored in the second memory and used by the second processor, including an index of positions for the plurality of probe light beams, a first set of fiber positions for the first optical fiber bundle at the entrance plane, a second set of fiber positions for the second optical fiber bundle at the exit plane, a first index of terminated fiber positions for the first optical fiber bundle as terminated on the elastomeric cap, a second index of terminated fiber positions for the second optical fiber bundle as terminated on the elastomeric cap, and a third index relating a fiber position in the second optical fiber bundle to a detector position in the optical detection system.

In a preferred embodiment, the functional NIRS system utilizes a data table stored in the second memory and used by the second processor to modulate the plurality of probe beams, comprising a series of time slots for illuminating the plurality of probe beams and a set of time slot assignments from the series of time slots for a set of optical fibers in the first optical fiber bundle. The data table further comprises a range of receive fibers in the second optical fiber bundle assigned to an optical fiber in the first optical fiber bundle. A subset of optical fibers in the first optical fiber bundle, with non-overlapping ranges of receive fibers, shares a time slot assignment.

In an alternate embodiment, the functional NIRS utilizes a data table stored in the second memory and used by the second processor to modulate the plurality of probe beams, comprising a set of modulation frequencies for modulating the plurality of probe beams and a set of modulation frequency assignments from the set of modulation frequencies for a set of optical fibers in the first optical fiber bundle. The data table further comprises a range of receive fibers in the second optical fiber bundle assigned to an optical fiber in the first optical fiber bundle. A subset of optical fibers in the first optical fiber bundle, with non-overlapping ranges of receive fibers, share a modulation frequency assignment.

A second embodiment of the functional NIRS imaging system for hemodynamic imaging of subcutaneous tissue includes a computer with a processor, a memory, a persistent storage device and a display. The system further comprises an elastomeric cap, an optical fiber bundle, terminating together at a first end plane and terminating dispersively on the inside surface of the elastomeric cap, comprising a set of transmit optical fibers and a set of receive optical fibers, a first light source producing a first light beam at a first wavelength and controlled by the computer, a second light source producing a second light beam at a second wavelength and controlled by the computer, an optical combiner combining the first light beam and the second light beam into a third light beam, an optical collimator collimating the third light beam into a fourth light beam, a modulation controller including a second processor and a second memory, and an optical modulation system, controlled by the modulation controller, which accepts the fourth light beam, converts the fourth light beam into a plurality of probe light beams, independently modulates each probe light beam in the plurality of probe light beams, programmatically directs each probe light beam in the plurality of probe light beams into a transmit optical fiber in the set of transmit optical fibers.

The functional NIRS imaging system programmatically directs a plurality of collected light beams from the set of receive optical fibers into an optical detection system, which is controlled by the first processor and connected to the first memory, and which accepts the plurality of collected light beams from the optical modulation system, converts the plurality of collected light beams into a time series of electronic images and stores the time series of electronic images into the memory.

A computer readable media including a first set of programmed instructions, when executed by the processor, converts the stored time series of electronic images into a set of hemoglobin oxygen saturation level maps, programmatically displays the set of hemoglobin oxygen saturation level maps on the display and stores the set of hemoglobin oxygen saturation level maps in the persistent storage device.

Also disclosed herein is a method for hemodynamic imaging of subcutaneous tissue utilizing a computer, with a first processor and a first memory, an optical modulator connected to a programmable modulation controller with a second processor and a second memory, and a detector array connected to the computer, the method providing for at least one optical fiber bundle including a set of transmit fibers terminating at the surface of an elastomeric cap and a set of receive fibers terminating at the surface of an elastomeric cap. The method further providing a collimated light beam, alternating the wavelength of the collimated light beam between wavelengths L1 and L2, dividing the collimated light beam into a set of probe beams in the optical modulator and modulating the set of probe beams with the optical modulator.

The method continues by transmitting the set of probe beams through the set of transmit fibers and through the elastomeric cap wherein each probe beam is transmitted primarily by a single optical fiber. Photons scattered from the subcutaneous tissue below the elastomeric cap into the set of receive fibers are collected and delivered to the detector array wherein each fiber in the at least one optical fiber bundle is imaged onto a subset of detectors in the detector array to form a set of image data.

The method continues by a group of processing steps including processing the set of image data to create two high resolution images of the subcutaneous tissue wherein the two high resolution images include a first high resolution image corresponding to the collimated light beam at the wavelength L1 and a second high resolution image corresponding to the collimated light beam at wavelength L2, and combining the two high resolution images together to create a hemoglobin oxygen saturation image of the subcutaneous tissue.

In a second embodiment, the method provides a transmit optical fiber bundle for the set of transmit fibers and a receive optical fiber bundle for the set of receive fibers.

In a third embodiment, the method includes mapping each receive fiber in the set of receive fibers to each image pixel in the detector array corresponding to the each receive fiber's position on the elastomeric cap, and delivering the photons from the set of receive fibers to the detector array with the optical modulator according to the mapping.

The method continues by determining a fiber map P which maps each transmit fiber in the set of transmit fibers to a probe beam in the set of probe beams, assigns the set of is assigned for each transmit fiber in the set of transmit fibers. The fiber map P is combined with a time slot map M to form a set of modulation matrices S. The time slot map M is stored with the fiber map P and the set of modulation matrices S in the programmable modulation controller.

The method includes configuring the collimated light beam with light at a wavelength L1, modulating the set of probe beams with the modulation matrix $S(t_n)$ during the first half of the nth time slot $t_n$, recording a first raw image in the detector array during the first half of the nth time slot $t_n$. The method continues by reconfiguring the collimated light beam with light at the wavelength L2, modulating the set of probe beams with the modulation matrix $S(t_n)$ during the second half of the nth time slot $t_n$ and recording a second raw image in the detector array during the second half of the nth time slot $t_n$.

The steps of collimating the light beam with light at wavelength L1, modulating the set of probe beams, recording a first raw image in the detector array, reconfiguring the collimated light with light at wavelength L2, modulating the set of probe beams and recording a second raw image in the detector array are repeated for all time slots resulting in a first set of raw images for wavelength L1 and a second set of raw images for wavelength L2.

The first set of raw images are combined into a set of intermediate images for the wavelength L1. The second set of raw images are combined into a set of intermediate images for wavelength L2. The set of intermediate images for wavelength L1 are further combined with the set of intermediate images for the wavelength L2 to arrive at a hemoglobin oxygen saturation image of the subcutaneous tissue.

The method includes a map function which converts an input set of raw images to physical dimensions of the elastomeric cap and maps an image pixel to a position on the elastomeric cap.

In another aspect of the map function, a range of receive fibers is associated to the kth transmit fiber in the set of transmit fibers. Then a kth intermediate image $F_{\lambda k}$ associated to the kth transmit fiber, is filtered out from the set of intermediate images based on the range of receive fibers.

The method provides for creating and applying a transformation matrix that incorporates a model of physical transformations for improving image resolution and for applying a set of instrument calibrations including optical fiber losses. The result of the transformation matrix is a pair of images $I_h$, one image for HbO and one image for Hb concentrations. A single hemoglobin oxygen saturation image of the subcutaneous tissue is determined from the $I_h$ by forming a ratio of HbO pixel values and (HbO+Hb) pixel values.

In another aspect of the method, the step of creating the transformation matrix includes incorporating reconstruction techniques to de-noise the first and second sets of intermediate images. In yet another aspect of the transformation matrix, a reconstruction technique is selected from the group consisting of: applying lower-level regularization in a Moore-Penrose inverse transformation, applying deblurring techniques based on Bayesian priors, applying synthetic aperture analysis and applying any combination thereof.

In yet another aspect of the method, the step of applying the transformation matrix is repeated to create a set of image pairs $I_h(d)$ for varying depths d and the step of determining hemoglobin oxygen saturation image is repeated to determine a three-dimensional hemoglobin oxygen saturation image.

A more detailed discussion of these embodiments and aspects of the embodiments are provided herein.

BRIEF DESCRIPTION OF THE DRAWINGS

The detailed description of the disclosure is best understood with reference to the drawings provided.

FIG. 5 is a calibration table related to the optical transmission.

FIG. 6 is a calibration table related to the optical detection.

DETAILED DESCRIPTION

Disclosed are a system and method for functional near infrared spectroscopy (fNIRS) that is useful for hemodynamics and provides a significant improvement over the prior art in resolution and frame rate of images.

Figure 1A:
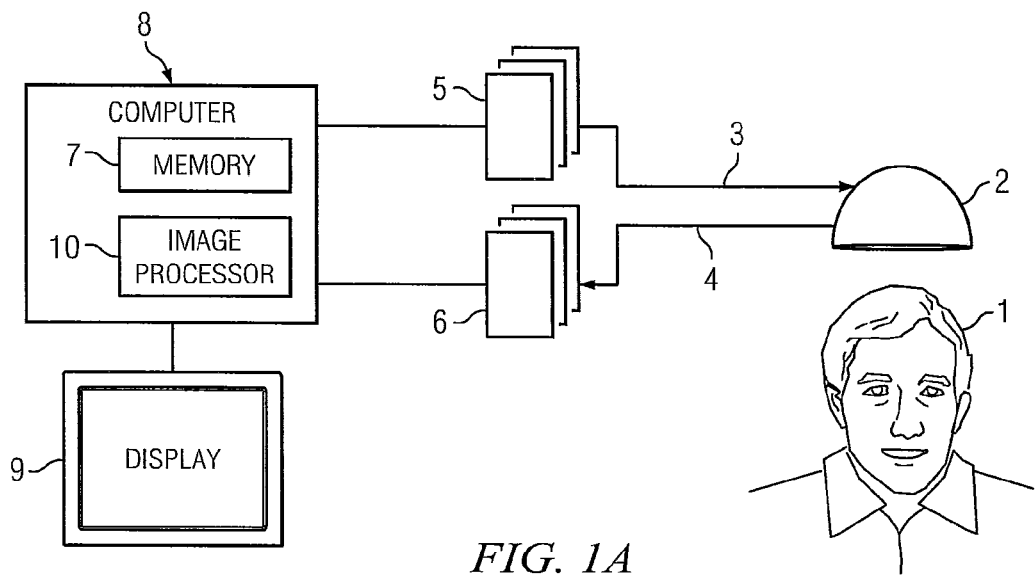
FIGS. 1A, 1B and 1C depict systems of the prior art.
Figure 1B:
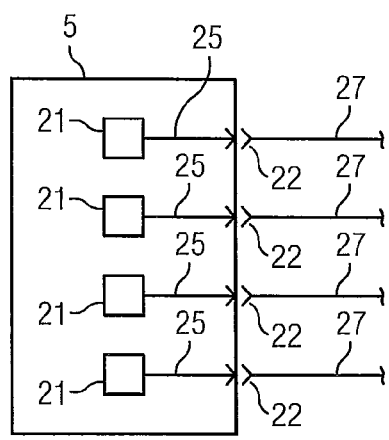
Figure 1C:
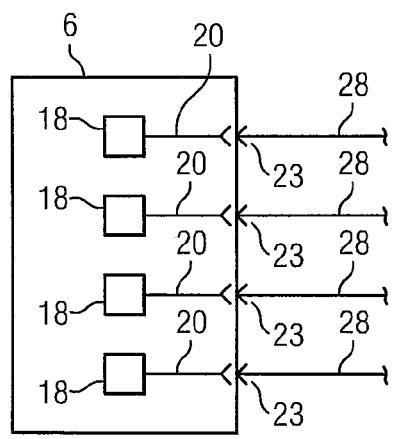
Figure 2:
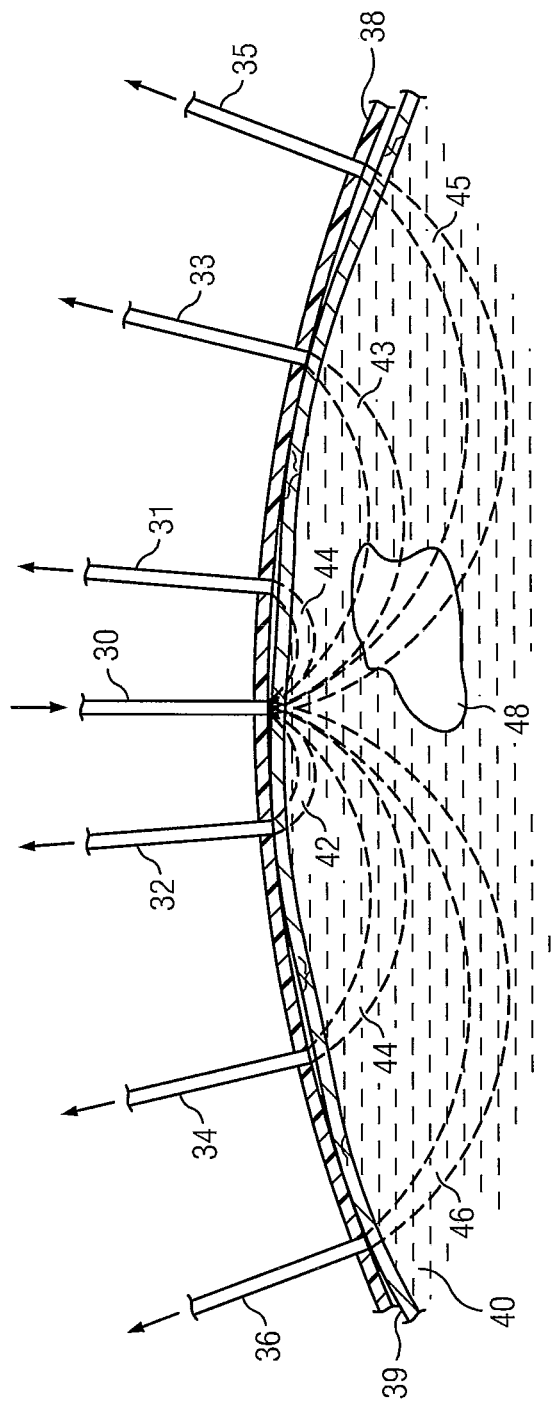
FIG. 2 is a diagram showing the propagation and scattering of light by subcutaneous matter from a transmit fiber to a set of receive fibers.
Figure 3:
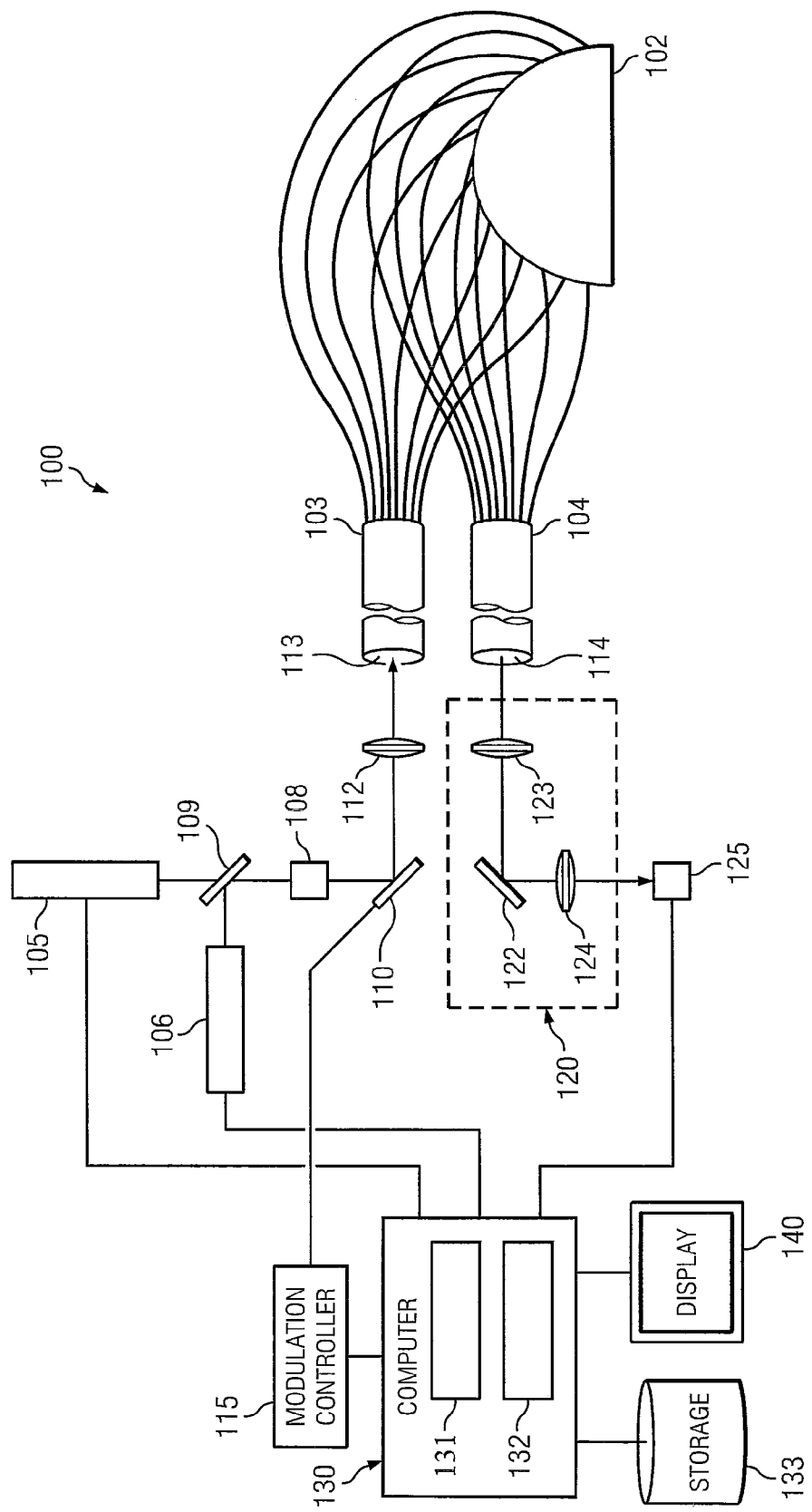
FIG. 3 is a block diagram of an fNIRS system according to a first embodiment.

Referring to FIG. 3, an fNIRS system 100 is shown. Light source 105 operates at a first wave length λ1 in the range of 690 nm and is positioned to impinge an incident beam on combiner 109. Light source 106 operates at a second wave length λ2 in the range of 830 nm and is positioned to impinge an incident beam on combiner 109. The wavelengths are chosen to be on different sides of the equi-absorption wavelength for oxygenated hemoglobin and deoxygenated hemoglobin that occurs near 800 nm. Combiner 109 combines the light beam from light source 105 with the light beam from a light source 106 into a transmit beam which is directed toward collimator 108. Collimator 108 expands and collimates the transmit beam and directs it toward modulator 110. Modulator 110 is a spatial light modulator such as a MEMS device. In the preferred embodiment, the MEMS device is a digital mirror device (DMD) available from Texas Instruments Corporation. The DMD device is a controllable two-dimensional ray of MEMS mirrors. Other types of special light modulators can be employed. Modulator 110 is logically connected to modulation controller 115 and responds to commands received from it.

Modulator 110 redirects the incident beam to lens 112. Lens 112 focuses the transmit beam onto transmit fiber bundle 103 at input termination plane 113. Transmit fiber bundle 103 in the preferred embodiment is a series of plastic fibers of diameter 0.5 mm to 1.0 mm. In the preferred embodiment, the number of transmit fibers in transmit fiber bundle 103 can range between 5,000 and 50,000 individual fibers.

Transmit fiber bundle 103 terminates in a distribution of individual fibers into elastomeric cap 102. Each of the fibers is fixed in the elastomeric cap and directs portions of the transmit beam toward the patient.

Scattered beams are received at individual fibers of receive fiber bundle 104 at elastomeric cap 102. Receive fiber bundle 104 terminates at output termination plane 114. Lens 123, lens 124 and reflector 122 cooperate to arrange and magnify the image received at termination plane 114 and focus it to photodetector array 125.

Each portion of the multiple portions of the transmit beam is preferably associated to a mirror device or cluster of mirrored devices in modulator 110. Lens 112 in combination with the adjustable mirror positions focuses the portion of light reflected from each mirror device to a single fiber at the input termination plane 113. The modulation of a single mirror device and associated fiber is preferably done to either focus all of the portion of light onto the single fiber or deflect the portion of light away from the system optics all together. The transmit-receive channels are isolated from other nearby transmit-receive pairs by modulation of transmit channels with, for example, Time Division Multiple Access (TDMA) or Frequency Division Multiple Access (FDMA). Each of these or a combination of these is useful in the invention.

Modulation controller 115 is programmed to modulate the mirror devices of modulator 110. In alternate embodiments, the modulation controller is programmed to modulate the optical elements to control light intensity of the multiple portions of the transmit beam, for example, to modulate cells of liquid crystal light modulator.

Photodetector array 125 is selected from the group of an array of avalanche photodiodes (APD), an array of silicon photodiodes, a cooled, high sensitivity solid state detector array, a multi-anode photomultiplier tube, a CMOS imaging device, and a charge coupled (CCD) imaging device. A multi-anode photomultiplier tube is preferably used for detector array 125.

Computer 130 includes electronic memory 131, such as random access memory, and persistent electronic storage 133, such as a hard drive. Computer programs are stored on persistent electronic storage 133 and loaded into electronic memory 131 to make computer 130 operable to perform the functions of the exemplary embodiments of the present invention. One set of such computer programs, image construction 132, operates to collect raw data from detector array 125, construct images relating to subcutaneous materials of the patient's brain from the raw data, and display the images and related results on display 140. In the preferred embodiment, the images of image construction 132 are image maps of hemoglobin oxygen saturation across the patient's brain at various depths within the patient's skull.

Figure 4:
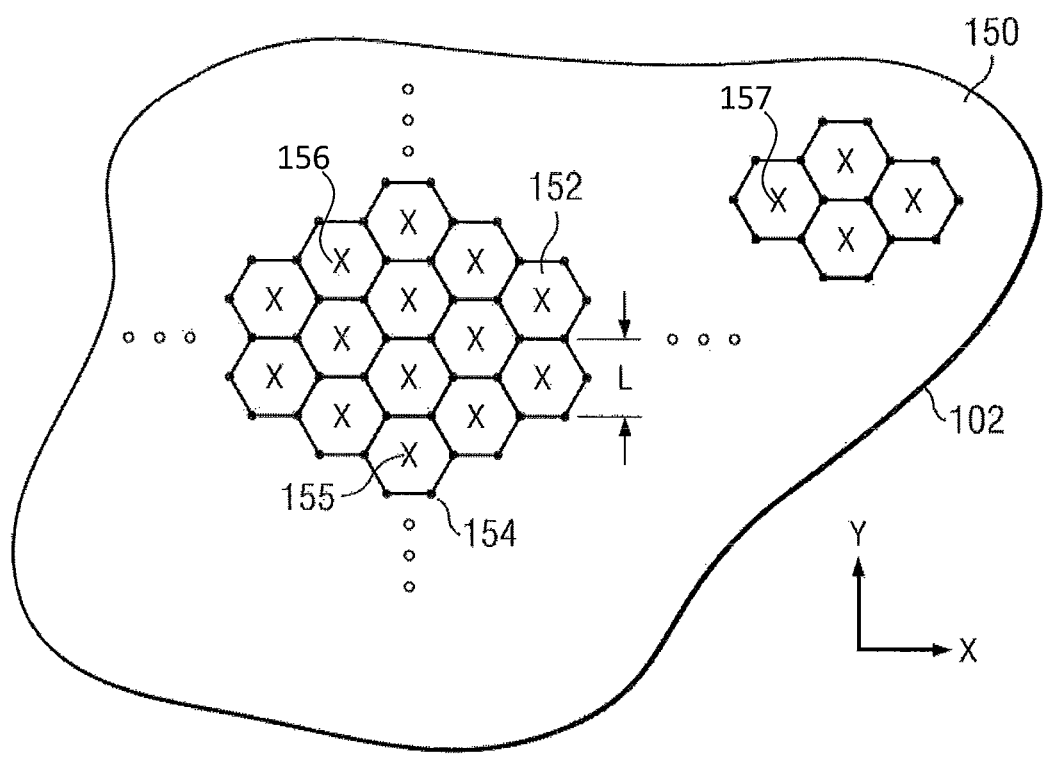
FIG. 4 is diagram of a section of an elastomeric cap of a preferred embodiment.

FIG. 4 is a diagram of a preferred embodiment elastomeric cap 102. Each dot in a set of dots 154 represents a vertex receive fiber position for receive fibers in the receive fiber bundle. Each X in a set of X's 155 mark a transmit fiber position for transmit fibers in the transmit fiber bundle. The receive fiber positions are arranged in a set of hexagonal units 152 which are packed together to share receive fibers. The transmit fiber positions are placed at the center of each hexagonal unit in the set of hexagonal units. The set of hexagonal units, receive fibers and transmit fibers are spread over the entire surface 150 of the elastomeric cap 102.

In the preferred embodiment the characteristic size L of a hexagonal unit is about 2 mm. Since the elastomeric cap covers approximately half of the patient's head, a typical elastomeric cap will contain about 4000 hexagonal units, 4000 transmit fibers and about 8500 receive fibers. Thus, a preferred transmit fiber bundle includes about 4000 optical fibers and a preferred receive fiber bundle includes about 8500 optical fibers. The ratio and numbers of transmit fibers and receive fibers can vary. The physical arrangement of the transmit and receive fibers can also vary. In general, it will be desirable to place fibers on 1 mm or less spacings in other to achieve mm or sub-millimeter resolution. In addition, thin, flexible, plastic fibers will easily thread through the hair of the subject under test.

It should be recognized that light transmitting through a particular transmit fiber into subcutaneous matter is not detectable at all receive fibers. For example, light entering at through a transmit fiber at cell 156 does not propagate to receive fibers at cell 157 because of the distance between cell 156 and cell 157. Light from a transmit fiber will be detected by a range of receive fibers. The range of receive fibers associated to a transmit fiber is determined by theoretical considerations or by empirical measurement at calibration.

The fNIRS system must be calibrated to include calibration data relating to (1) an indexing of positions of DMD mirror devices in relation to lateral positions of the portions of the transmit beam in the transmit termination plane, (2) the position of fibers in the receive termination plane as imaged on the image plane, (3) an indexing of transmit fiber positions as terminated on the elastomeric cap in relation to the lateral positions of each transmit fiber in the transmit termination plane, and (4) an indexing of receive fiber positions as terminated on the elastomeric cap in relation to the lateral positions of each receive fiber in the receive termination plane, (5) an indexing of each receive fiber upon a detector pixel or set of detector pixels on the receiving array.

FIG. 5 is a calibration table describing the calibration aspects of the optical transmission components. Calibration table 160 includes one row for each transmit fiber in the transmit fiber bundle. Each row has a set of columns of associated calibration data. Column 161 provides an index to each transmit fiber. Column 162 provides an association between a DMD mirror device and an associated transmit fiber. The association to the DMD mirror device in a preferred embodiment is a pair of indices, one index for each dimension of the device, as in a matrix position. Column 163 provides a DMD mirror x-position. The DMD mirror x-position correlates to a voltage that when applied to the DMD mirror device in one dimension connects a light path to the associated transmit fiber. Column 164 provides a DMD mirror y-position. Similarly, the DMD mirror y-position is a voltage that when applied to the DMD mirror device in the second dimension connects a light path to the associated transmit fiber. Column 165 is an x-position of the associated transmit fiber on the elastomeric cap. Column 166 is a y-position of the associated transmit fiber on the elastomeric cap. Column 167 is a pixel x-position of the associated transmit fiber within a reconstructed image of the elastomeric cap. Column 168 is a pixel y-position of the associated transmit fiber within a reconstructed image of the elastomeric cap. Column 170 is the optical loss measured through the system for the associated transmit fiber. In a preferred embodiment, where time division multiplexing is used, column 171 contains a time slot assignment for the associated transmit fiber. Column 172 contains a list of receive fiber indices in the range of the associated transmit fiber.

In an alternate embodiment where frequency division multiplexing is used, column 171 contains a modulation frequency assignment for the associated transmit fiber.

FIG. 6 is a calibration table describing the calibration aspects of the optical detection components. Calibration table 180 includes one row for each receive fiber in the receive fiber bundle. Each row has a set of columns of associated calibration data. Column 181 provides an index to each receive fiber. Column 182 is a x-position of an associated receive fiber on the elastomeric cap. Column 183 is a y-position of the associated receive fiber on the elastomeric cap. Column 184 is a pixel x-position for the associated receive fiber within a reconstructed image of the elastomeric cap. Column 185 is a pixel y-position for the associated receive fiber within a reconstructed image of the elastomeric cap. Column 186 is the optical loss measured through the system for the associated receive fiber.

Calibration of the elastomeric cap is performed by imaging the inner surface of the elastomeric cap, causing light from a light source to propagate down individual fibers, and indexing the position of the fiber from which light emanates.

Figure 7:
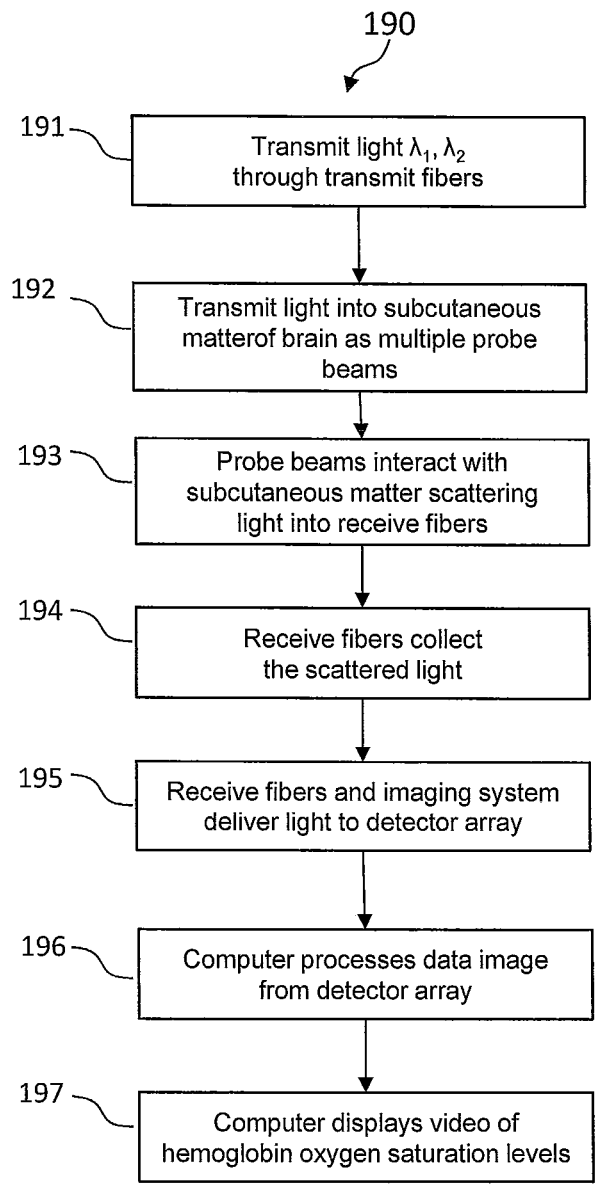
FIG. 7 is a flow chart for the overall operation of an fNIRS system.

FIG. 7 shows an operational flow diagram 190 of the apparatus in operation. At step 191, the fNIRS system alternatively transmits collimated light of wavelengths $\lambda 1$ and $\lambda 2$ through a set of transmit fibers in transmit fiber bundle, and at step 192 the collimated light is split into a plurality of probe light beams and is further transmitted through the elastomeric cap, and into the subcutaneous matter of the patient. At step 193, the plurality of probe light beams experience optical scattering and absorption from the subcutaneous matter to produce a scattered light. At step 194, the scattered light is collected by a set of receive fibers of the receive fiber bundle. At step 195, the scattered light, when collected, is delivered by each receive fiber and by the optical imaging system onto the detector array in predefined detector positions related to the order of receive fibers in the receive fiber bundle. At step 196, the detector array converts the scattered, collected and delivered photons of the scattered light into image data which the computer collects from the detector, reorders according to physical receive fiber position on the elastomeric cap and further processes to form a time series of image frames of hemoglobin oxygen saturation level maps. At step 197, the time series of image frames of hemoglobin oxygen saturation levels are displayed as a real-time video on a display. These general steps are described in greater detail in the Figures that follow.

Figure 8:
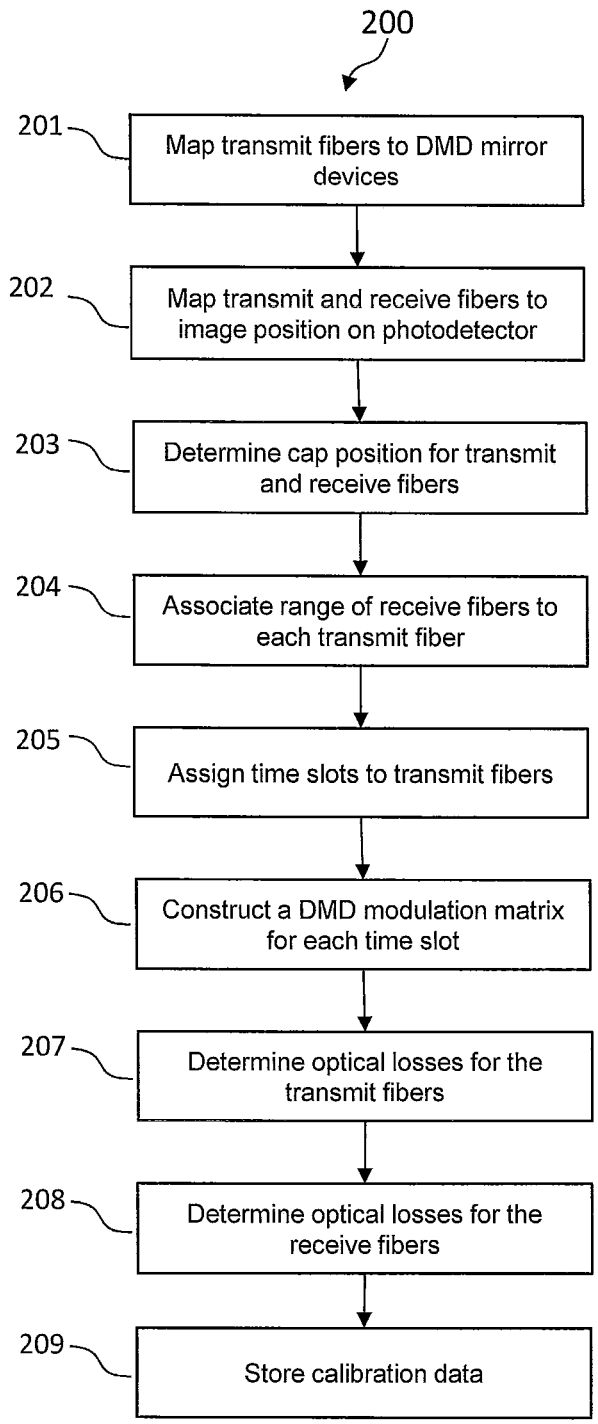
FIG. 8 is a flow chart of a calibration method.

Referring to FIGS. 5 and 8, calibration process 200 of the optical transmission is shown. At step 201, an assignment is created which maps the set of transmit fibers to a set of DMD mirror devices. Step 201 creates and columns 161-164 of calibration table 160. At step 202, another assignment is created which maps the set of receive fibers and the set of transmit fibers to a set of image pixel coordinates. Step 202 creates columns 181, 184 and 185 of calibration table 180 and columns 167 and 168 of table 160. At step 203, cap position coordinates are determined for the set of transmit fibers and cap position coordinates are determined for the set of receive fibers. Step 203 creates columns 165-166 of calibration table 160 and columns 182-183 of calibration table 180. At step 204, associated ranges of receive fibers are associated to the set of transmit fibers which results in column 172 being populated in calibration table 160. At step 205, a time slot in a series of time slots is assigned to each transmit fiber. In a preferred embodiment, time slots are assigned to transmit fibers such that their associated ranges do not overlap in any given time slot. Step 205 populates column 171 of calibration table 160. At step 206, a set of DMD modulation matrices are constructed for the series of time slots, each DMD modulation matrix corresponding to a time slot.

At step 207, transmit fiber optical losses are determined for each transmit fiber in the set of transmit fibers. At step 208, receive fiber optical losses are determined for each receive fiber in the set of receive fibers. At step 209, the calibration data generated in steps 201-208 is stored in the modulation controller.

In a first example of time slot assignment, if the range of each transmit fiber is the entire set of receive fibers, then a unique time slot is assigned to each transmit fiber.

In a second example of time slot assignment, 10 different transmit fibers share a single time slot. For example, suppose there are N=4000 transmit fibers in the elastomeric cap with N hexagonal units of receive fibers. Also suppose the range of one transmit fiber is about 2 cm resulting in about M=400 cells and their corresponding receive fibers in range of the one transmit fiber. Then, there will be about N/M=10 non-overlapping ranges associated. About 400 time slots will be required to image all of the N=4000 transmit fibers in the elastomeric cap.

Of course, other numbers of transmit fibers can share a single time slot.

In an alternate embodiment, calibration process 200 is performed for a set of modulation frequencies rather than a series of time slots wherein the set of modulation frequencies are assigned to the set of transmit fibers in column 171 of calibration table 160. A unique modulation frequency is assigned to a subset of transmit fibers having non-overlapping ranges of receive fibers.

Figure 9:
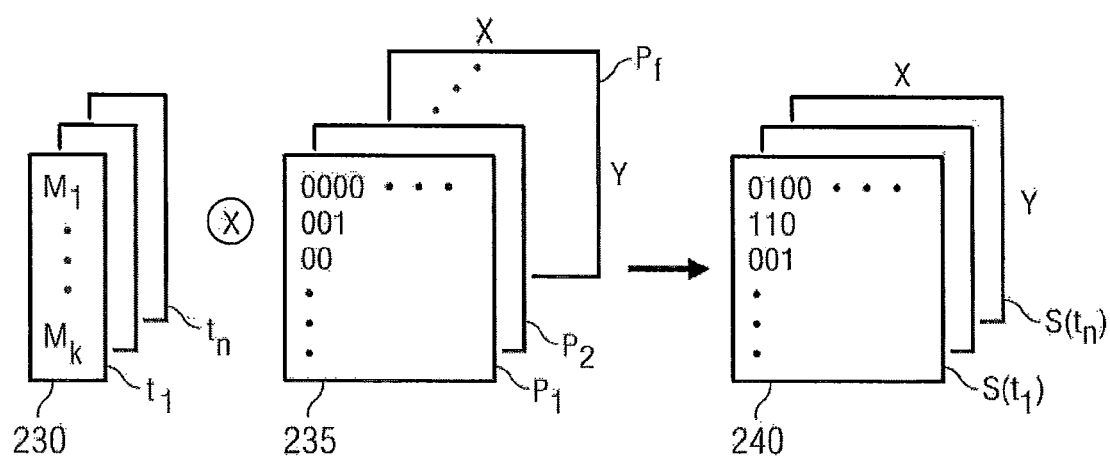
FIG. 9 is block diagram depicting the mathematical operations related to a processing method.

FIG. 9 describes the set of DMD modulation matrices in greater detail. There are f transmit fibers in the transmit fiber bundle. From the calibration table 160, a fiber modulation matrix $M_{kn}$ 230 is generated: the kth row of $M_{kn}$ representing a transmit fiber index k and the nth column of $M_{kn}$ representing a time slot at time $t_n$. The elements of $M_{kn}$ are either 1 (one) or 0 (zero). If $M_{kn}=1$, then the kth fiber is transmitting light in the nth time slot at time $t_n$. If $M_{kn}=0$, then the kth fiber is not transmitting light in the nth time slot at time $t_n$. The set of fiber positions are described by a set of positional matrices $P_f$ 235, one positional matrix $P_k$ for each transmit fiber k, where the x and y DMD matrix assignment is a "1" in the associated transmit fiber position. The fiber modulation matrix 230 and the set of positional matrices $P_f$ 235 are combined to from a set of DMD modulation matrices S(t) 240 according to:

$$S(t_n) = \sum_{i=1}^{f} P_i \cdot M_i(t_n) \quad (1)$$

where $S(t_n)$ is the DMD modulation matrix for modulating the DMD mirror devices in a time slot at time $t_n$.

Figure 10:
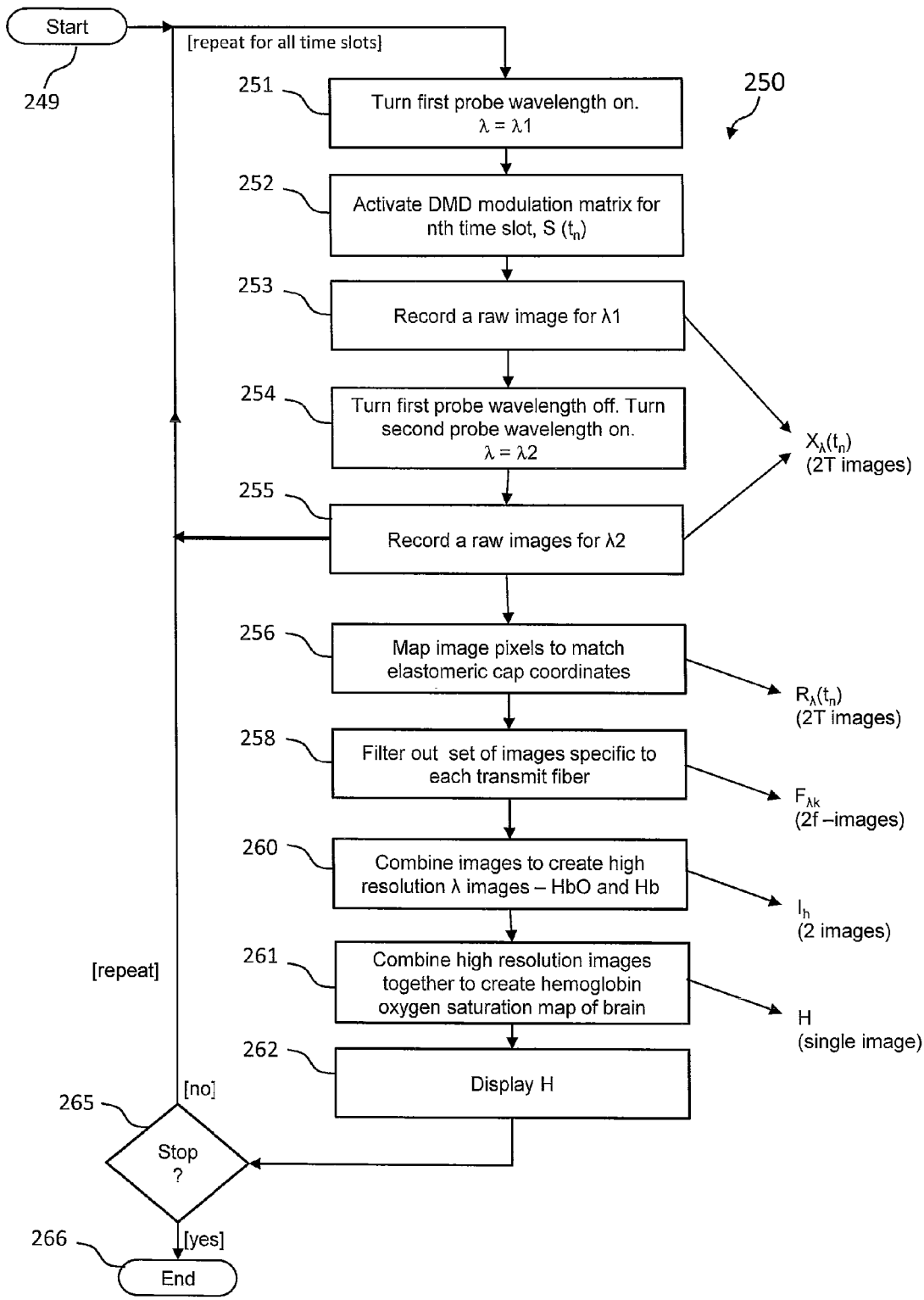
FIG. 10 is a flow chart of an optical detection and processing method used during operation of an fNIRS system.
Figure 11:
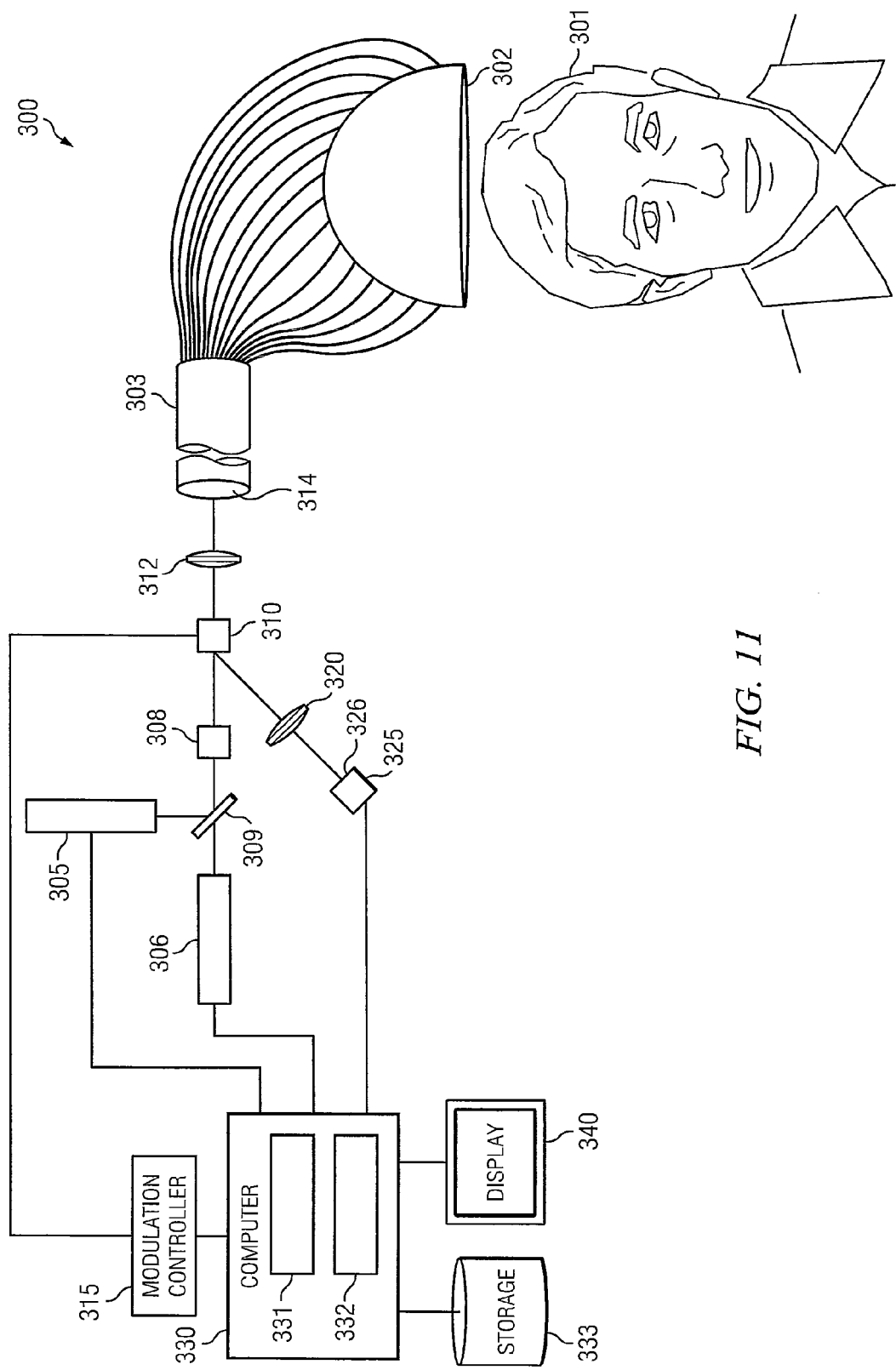
FIG. 11 is a block diagram of an fNIRS according to an alternate embodiment.

FIG. 10 is flow chart of optical detection and processing method 250. The apparatus of FIG. 3 or FIG. 11 is suitable to carry out the method. The assumptions surrounding the steps of optical detection and processing method 250 are that there are f fibers in the transmit fiber bundle and T time slots. There are two transmit wavelengths λ1 and λ2, where λ1 signifies a first probe wavelength generated, preferably chosen to be 690 nm, and λ2 signifies a second probe wavelength, preferably chosen to be 830 nm.

At step 249, the method begins by looping through steps 251-255. At step 251, the first probe wavelength is turned on during the first half of the nth time slot. At step 252, the DMD modulation matrix element $S(t_n)$ is activated by the modulator and a set of probe beams, at wavelength λ1, are focused onto the set of transmit fibers in the transmit fiber bundle and sent to the patient via the transmit fiber bundle. Light scatters from subcutaneous matter and is collected into set of receive fibers in the receive fiber bundle and focused onto the photodetector array. At step 253, a raw image $X_{\lambda,1}(t_n)$ for the first probe wavelength is recorded by the photodetector array and transferred to the computer memory where it is stored.

At step 254, the first probe wavelength is turned off and the second probe wavelength is turned on during the second half of the nth time slot. The set of probe beams, now at wavelength λ2, are focused onto the set of transmit fibers in the transmit fiber bundle and sent to the patient via the transmit fiber bundle. Light scatters from subcutaneous matter and is collected into set of receive fibers in the receive fiber bundle and focused onto the photodetector array. At step 255, a raw image $X_2(t_n)$ for the second probe wavelength is recorded by the photodetector array during the second half of the nth time slot and transferred to the computer memory where it is stored. Steps 251-255 are repeated for all time slots until a set of 2T images $X_\lambda(t_n)$, for n=1, 2, . . . T and λ=λ1 and λ2, are collected and where each raw image $X_\lambda(t_n)$ has the pixel dimensions of the photodetector array.

At step 256, the set of raw images are mapped into the coordinates of the elastomeric cap to create a set of intermediate images $R_{\lambda,k}$ according to:

$$R_\lambda(t_n) = map(X_\lambda(t_n)). \quad (2)$$

Step 256 can employ a simple pixel rearrangement in some embodiments, while in other embodiments step 256 performs a scaling procedure to map pixels to real dimensions. Step 256 uses the information stored in columns 182, 183, 184 and 185 of table 180 to map an image pixel to an elastomeric cap position. The output of step 256 is the set of intermediate images $R_\lambda(t_n)$ containing 2T images.

At step 258 the set of intermediate images $R_\lambda(t_n)$ are processed according to:

$$F_{\lambda,k}[i,j] = R_\lambda(t_k)[i,j] \cdot Q_k[i,j] \quad (3)$$

where the set of final images $F_{\lambda,k}$ is processed for wavelengths λ=λ1 and λ2, for k=1 to f transmit fibers, and where $Q_k$ is an area filter of image pixel coordinates associated to the range of receive fibers for the kth transmit fiber. The indexes i and j range over the pixels of the sets of intermediate images and the time slot $t_k$ is the time slot assigned to the kth transmit fiber.

In a first embodiment, the values of $Q_k$ are 1 (one) or 0 (zero). In other embodiments, a smoothing filter can be applied. Area filter $Q_k$ for the kth fiber is constructed from the calibration tables 160 and 180 comprising an enclosed area of image pixels that is set equal to 1 (one) and a remaining area of image pixels that is set equal to 0 (zero). For the kth transmit fiber, a list of receive fiber indices is provided in column 172 of table 160. The enclosed area of image pixels corresponds to all image pixel coordinates inside an area bounded by the pixel coordinates of receive fibers in the list of receive fiber indices. The pixel coordinates are given in calibration table 180 columns 181, 184 and 185.

Step 258 results in a set of final images containing 2f images, wherein each final image has dimensions of the photodetector array and each final image corresponds specifically to the optical response of subcutaneous matter to a single transmit fiber.

At step 260 the set of final images are further combined into two high resolution images, one image representing HbO concentration and one image representing Hb concentration according to the transformation:

$$I_h = A_h F_{\lambda,k} \quad (4)$$

where the transformation matrix $A_h$ incorporates the optical physics of combining multiple images at two wavelengths λ, normalizing the image according to the optical losses at each wavelength as contained in tables 160 and 180, and by determining extinction ratios of HbO and Hb, and calculating concentrations for h=HbO and Hb. It is possible to incorporate many physical and mathematical optimizations into the transformation matrix $A_h$. Some examples are: applying image re-construction techniques to de-noise the images such as the use of lower levels of regularization in a Moore-Penrose inverse, applying deblurring techniques based on Bayesian priors to create a super-resolution image, and applying synthetic aperture analysis to speed the computation and to allow for further increase in image resolution. The foregoing techniques can be applied in combination.

In an alternate embodiment, the transformation matrix $A_h$ incorporates the filtering function $Q_k$ of step 258 and operates directly on the set of intermediate images $R_\lambda(t_n)$ to form the two high resolution images $I_h$.

The output of step 260 is two high resolution images $I_h$ of the scattering return from subcutaneous matter in the patient's brain at the two probe wavelengths. In an alternate embodiment, multiple images $I_h$ can be selectively created at differing depths for HbO and Hb concentration at the output of step 260 by applying different matrices $A_h$ corresponding to gathering optical information at multiple depths within the patient's brain.

At step 261, the two high resolution images $I_h$ are further combined to create a single hemoglobin oxygen saturation image, H, of the patient's brain by forming a ratio of the pixel values in the $I_{HbO}$ image to the pixel values in the summed ($I_{Hb} + I_{HbO}$) image. The output of step 261 is a single two-dimensional image. In the alternate embodiment, step 261 is repeated for the multiple images to create hemoglobin oxygen saturation maps at different depths in the patient's brain. The output of the alternate embodiment is a three-dimensional image. At step 262, the two-dimensional hemoglobin saturation image is displayed on the display connected to the computer. In the alternate embodiment a three-dimensional image of hemoglobin saturation is displayed.

At step 265, the system checks if an operator has requested that the imaging run stop. If stopped, then the optical detection and processing method 250 ends at step 266, otherwise the optical detection and processing method 250 repeats at step 252.

FIG. 11 shows a second embodiment of an fNIRS system 300. The system comprises two light sources: light source 305 operating at a first wavelength, λ1 and light source 306 operating at a second wavelength λ2, beam combiner 309 for combining a light beam from light source 305 with a light beam from light source 306 into a transmit beam, collimator 308 for expanding and collimating the transmit beam, bidirectional fiber bundle 303, spatial light modulator 310 for modulating multiple portions of the transmit beam, lens system 312 for focusing the multiple portions of the transmit beam onto multiple fibers of bidirectional fiber bundle 303 at optical termination plane 314, elastomeric cap 302 on which bidirectional fiber bundle 303 is fastened and optically terminated near the skull of patient 301, photodetector array 325, imaging system 320 for imaging the optical termination plane 314 of bidirectional fiber bundle 303 onto photodetector array 325, computer 330 for processing images, a display 340 for displaying images, and modulation controller 315 for controlling spatial light modulator 310.

The wavelength λ1 is preferably 690 nm and wavelength λ2 is preferably 830 nm. The light sources are preferably lasers, and the spatial light modulator is preferably selected from group of a MEMS device and a liquid crystal light modulator. The optical fibers in bidirectional fiber bundle 303 are preferably low loss (per-fluorinated) plastic fibers of diameter 0.5 mm to 1.0 mm.

Each portion of the multiple portions of the transmit beam is preferably associated with a modulated element of spatial light modulator 310. Lens system 312 in combination with spatial light modulator 310 focuses the light ray from each modulated element to a single fiber at the optical termination plane 314.

Imaging system 320 is preferably a lens system, in combination with spatial light modulator 310, arranged to create a magnified image of the optical termination plane 314 of the bidirectional fiber bundle on image plane 326 of photodetector array 325.

Modulation controller 315 is programmed to modulate the spatial light modulator so as to transmit light applied to the bidirectional fiber bundle and for receiving light collected by the bidirectional fiber bundle, redirecting the receive light into the imaging system 320.

Computer 330 includes processors, field programmable gate arrays, electronic memory 331, such as random access memory, and persistent electronic storage 333, such as a hard drive. Computer programs are stored on persistent electronic storage 333 and loaded into electronic memory 331 to make computer 330 operable to perform the functions of the exemplary embodiments of the present invention. One set of such computer programs, image construction 332, operates to collect raw data from photodetector array 325, construct images relating to subcutaneous materials of the patient's brain from the raw data, and display the images and related results on display 340. In the preferred embodiment, the images of image construction 332 are image maps of hemoglobin oxygen saturation across the patient's brain at various depths within the patient's skull.

Referring to FIG. 3, in a third embodiment of the present invention, a spatial light modulator is included in the optical imaging system 120. The spatial light modulator is programmed to redirect the light from each fiber in the receive fiber bundle to an image pixel which closely corresponds to a correct position of the receive fiber as it is terminated on the elastomeric cap. The third embodiment is configured to optically accomplish the step 258 of optical detection in processing method 250.

Other embodiments are envisioned. As for the apparatus, light sources are selected from the group of lasers, LEDs, broad area devices all of which operate at typical NIRS wavelengths. Modulation of the transmit beam can be effected at the light sources for certain aspects, such as synchronization. In other aspects, wherein there is an array of light sources, the array of light sources can be individually modulated instead of using the spatial light modulator. Other modulation schemes can be selected in which timeslot and frequency, respectively, are reused across the area of the elastomeric cap providing distances between transmit fibers are large enough to avoid crosstalk. As for detection, the detector bundle can be directly pigtailed to an array of photodetector devices. Other imaging devices such as high resolution cameras may also be employed. The optical imaging system can utilize lenses, lens array prisms, and other known optical components used in massively connected optical systems. Elastomeric cap materials include any shape memory materials including polymers that provide for automated threading of fibers into the scalp of the patient.

The invention claimed is:

1. A system for imaging of subcutaneous tissue comprising:
   a first processor;
   a first light source, connected to the first processor, producing a first light beam;
   a second light source, connected to the first processor, producing a second light beam;
   an optical combiner, receiving the first light beam and the second light beam, and producing a third light beam;
   a modulator, connected to the first processor, receiving the third light beam and producing a plurality of probe light beams;
   a set of input fibers, receiving the plurality of probe light beams;
   each probe light beam of the plurality of probe light beams directed to a corresponding fiber of the set of input fibers;
   a cap, adjacent the subcutaneous tissue, having an input set of locations and a set of output locations, connected to the set of input fibers;
   each fiber of the set of input fibers corresponding to an input location of the set of input locations;
   a set of output fibers, connected to the cap, receiving a plurality of reflected light beams from the subcutaneous tissue;
   each fiber of the set of output fibers corresponding to an output location of the set of output locations;
   an optical detector array, connected to the processor and the set of output fibers, converting the plurality of reflected light beams into a set of signals;
   the processor programmed to:
      convert the set of signals into a time series of electronic images;
      convert the time series of electronic images into a set of hemoglobin oxygen saturation level maps;

a modulation controller to programmed to modulate optical elements of the modulator to control light intensity of the multiple portions of the third light beam;

wherein the modulator further comprises a spatial light modulator and an optical lens, the spatial light modulator further comprises a MEMS digital mirror device, and the MEMS digital mirror device comprises a controllable two-dimensional ray of MEMS mirrors; and, wherein the modulation controller is further programmed to modulate the spatial light modulator to transmit and apply the third light beam to a bidirectional fiber bundle that is formed from the set of input fibers and the set of output fibers and is further programmed to modulate the spatial light modulator to receive and redirect the reflected light beams that are collected by the bidirectional fiber bundle into the optical detector array.

* * * * *